United States Patent
Young et al.

(10) Patent No.: US 9,358,317 B2
(45) Date of Patent: Jun. 7, 2016

(54) ACIDIC PROCESSES TO PREPARE ANTIMICROBIAL CONTACT LENSES

(75) Inventors: Kent Young, Jacksonville, FL (US); Osman Rathore, Jacksonville, FL (US); Nayiby Alvarez-Carrigan, St. Augustine, FL (US); David Turner, Jacksonville, FL (US); Frank Neely, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 1118 days.

(21) Appl. No.: 13/007,776

(22) Filed: Jan. 17, 2011

(65) Prior Publication Data

US 2011/0111001 A1 May 12, 2011

Related U.S. Application Data

(63) Continuation of application No. 11/923,685, filed on Oct. 25, 2007, now abandoned.

(60) Provisional application No. 60/863,583, filed on Oct. 31, 2006.

(51) Int. Cl.
*A61L 12/08* (2006.01)
*G02B 1/04* (2006.01)

(52) U.S. Cl.
CPC .............. *A61L 12/088* (2013.01); *G02B 1/043* (2013.01)

(58) Field of Classification Search
CPC ............................ A61L 12/088; G02B 1/043
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 3,808,178 A | 4/1974 | Gaylord | |
| 4,113,224 A | 9/1978 | Clark et al. | |
| 4,120,570 A | 10/1978 | Gaylord | |
| 4,136,250 A | 1/1979 | Mueller et al. | |
| 4,139,513 A | 2/1979 | Tanaka et al. | |
| 4,139,692 A | 2/1979 | Tanaka et al. | |
| 4,153,641 A | 5/1979 | Deichert et al. | |
| 4,182,822 A | 1/1980 | Chang | |
| 4,189,546 A | 2/1980 | Deichert et al. | |
| 4,197,266 A | 4/1980 | Clark et al. | |
| 4,254,248 A | 3/1981 | Friends et al. | |
| 4,259,467 A | 3/1981 | Keogh et al. | |
| 4,260,725 A | 4/1981 | Keogh et al. | |
| 4,261,875 A | 4/1981 | LeBoeuf | |
| 4,276,402 A | 6/1981 | Chromecek et al. | |
| 4,301,012 A | 11/1981 | Puckett | |
| 4,327,203 A | 4/1982 | Deichert et al. | |
| 4,330,383 A | 5/1982 | Ellis et al. | |
| 4,341,889 A | 7/1982 | Deichert et al. | |
| 4,343,927 A | 8/1982 | Chang | |
| 4,355,147 A | 10/1982 | Deichert et al. | |
| 4,410,442 A | 10/1983 | Lucas et al. | |
| 4,450,264 A | 5/1984 | Cho | |
| 4,463,149 A | 7/1984 | Ellis | |
| 4,486,577 A | 12/1984 | Mueller et al. | |
| 4,495,313 A | 1/1985 | Larsen | |
| 4,525,563 A | 6/1985 | Shibata et al. | |
| 4,543,398 A | 9/1985 | Bany et al. | |
| 4,605,712 A | 8/1986 | Mueller et al. | |
| 4,661,575 A | 4/1987 | Tom | |
| 4,680,336 A | 7/1987 | Larsen et al. | |
| 4,703,097 A | 10/1987 | Wingler et al. | |
| 4,711,943 A | 12/1987 | Harvey, III | |
| 4,725,277 A | 2/1988 | Bissonette | |
| 4,731,079 A | 3/1988 | Stoy | |
| 4,743,447 A * | 5/1988 | Le Rouzic et al. | ............ 424/616 |
| 4,837,289 A | 6/1989 | Mueller et al. | |
| 4,863,464 A | 9/1989 | Dusek | |
| 4,871,785 A | 10/1989 | Froix | |
| 4,872,876 A | 10/1989 | Smith | |
| 4,889,664 A | 12/1989 | Kindt-Larsen et al. | |
| 4,954,586 A | 9/1990 | Toyoshima et al. | |
| 4,954,587 A | 9/1990 | Mueller | |
| 5,010,141 A | 4/1991 | Mueller | |
| 5,034,461 A | 7/1991 | Lai et al. | |
| 5,039,459 A | 8/1991 | Kindt-Larsen et al. | |
| 5,057,578 A | 10/1991 | Spinelli | |
| 5,070,215 A | 12/1991 | Bambury et al. | |
| 5,314,960 A | 5/1994 | Spinelli et al. | |
| 5,336,797 A | 8/1994 | McGee et al. | |
| 5,346,946 A | 9/1994 | Yokoyama et al. | |
| 5,358,995 A | 10/1994 | Lai et al. | |
| 5,371,147 A | 12/1994 | Spinelli et al. | |
| 5,387,632 A | 2/1995 | Lai et al. | |

(Continued)

FOREIGN PATENT DOCUMENTS

| | | |
|---|---|---|
| DE | 10024363 A1 | 11/2001 |
| EP | 406161 B1 | 2/1995 |

(Continued)

OTHER PUBLICATIONS

Becker et al, The Use of High Accuracy NAA for the Certification of NIST Botanical Standard Reference Materials, Journal of Radioanalytical and Nuclear Chemistry, vol. 160, No. 1. 1992, pp. 41-53.

Becker et al, Use of INAA, PGAA, and RNAA to Determine 30 Elements for Certification of an SRM: Tomato Leaves, 1573a, Journal of Radioanalytical and Nuclear Chemistry, vol. 179, No. 1 (1994) pp. 149-154.

Elimelech et al, "Particle deposition and aggregation, measurement, modeling and simulation" pp. 54-55. Butterworth Heinemann, Oxford 1995.

James, T.H. "The theory of the photographic process", 4th Ed. Eastman Kodak Company, 1977, pp. 31-32.

PCT International Search Report, dated Jul. 15, 2008, for PCT Int'l Appln. No. PCT/US2007/082597.

*Primary Examiner* — Sean Basquill
(74) *Attorney, Agent, or Firm* — Karen A. Harding

(57) ABSTRACT

This invention relates to antimicrobial lenses containing metals and methods for their production.

16 Claims, 2 Drawing Sheets

(56) References Cited

U.S. PATENT DOCUMENTS

| | | |
|---|---|---|
| 5,451,617 A | 9/1995 | Lai et al. |
| 5,486,579 A | 1/1996 | Lai et al. |
| 5,710,302 A | 1/1998 | Kunzler et al. |
| 5,714,557 A | 2/1998 | Kunzler et al. |
| 5,760,100 A | 6/1998 | Nicolson et al. |
| 5,776,999 A | 7/1998 | Nicolson et al. |
| 5,789,461 A | 8/1998 | Nicolson et al. |
| 5,807,944 A | 9/1998 | Hirt et al. |
| 5,849,811 A | 12/1998 | Nicolson et al. |
| 5,908,906 A | 6/1999 | Kunzler et al. |
| 5,944,853 A | 8/1999 | Molock et al. |
| 5,958,440 A | 9/1999 | Burrell et al. |
| 5,962,548 A | 10/1999 | Vanderlaan et al. |
| 5,965,631 A | 10/1999 | Nicolson et al. |
| 5,981,615 A | 11/1999 | Meijs et al. |
| 5,981,675 A | 11/1999 | Valint, Jr. et al. |
| 5,998,498 A | 12/1999 | Vanderlaan et al. |
| 6,020,445 A | 2/2000 | Vanderlaan et al. |
| 6,039,913 A | 3/2000 | Hirt et al. |
| 6,087,415 A | 7/2000 | Vanderlaan et al. |
| 6,585,768 B2 | 7/2003 | Hamano et al. |
| 7,319,133 B2 | 1/2008 | Brame |
| 2003/0095230 A1 | 5/2003 | Neely et al. |
| 2004/0150788 A1* | 8/2004 | Andersson et al. ....... 351/160 R |
| 2005/0008676 A1 | 1/2005 | Qui et al. |

FOREIGN PATENT DOCUMENTS

| | | |
|---|---|---|
| JP | 2000107277 | 5/1994 |
| JP | 200010055 | 1/2000 |
| JP | 2000016905 | 1/2000 |
| JP | 6123860 | 4/2000 |
| TW | 200505510 | 2/2005 |
| WO | 9421698 A1 | 9/1994 |
| WO | 9927978 A1 | 6/1999 |
| WO | 9929750 A1 | 6/1999 |
| WO | 0022459 A1 | 4/2000 |
| WO | 0022460 A1 | 4/2000 |
| WO | 0026698 A1 | 5/2000 |
| WO | 02062402 A1 | 8/2002 |
| WO | 03011351 A2 | 2/2003 |
| WO | 03022321 A2 | 3/2003 |
| WO | 2004047878 A1 | 6/2004 |
| WO | 2004047879 A2 | 6/2004 |
| WO | 2006012000 A1 | 2/2006 |

* cited by examiner

ACIDIC PROCESSES TO PREPARE ANTIMICROBIAL CONTACT LENSES

RELATED APPLICATION

This application is a continuation application of U.S. patent application Ser. No. 11/923,685, filed Oct. 25, 2007 now abandoned which is a non-provisional of U.S. Ser. No. 60/863,583, filed on Oct. 31, 2006, now abandoned.

FIELD OF THE INVENTION

This invention relates to methods of preparing antimicrobial lenses

BACKGROUND OF THE INVENTION

Contact lenses have been used commercially to improve vision since the 1950s. The first contact lenses were made of hard materials. They were used by a patient during waking hours and removed for cleaning. Current developments in the field gave rise to soft contact lenses, which may be worn continuously, for several days or more without removal for cleaning. Although many patients favor these lenses due to their increased comfort, these lenses can cause some adverse reactions to the user. The extended use of the lenses can encourage the buildup of bacteria or other microbes, particularly, Pseudomonas aeruginosa, on the surfaces of soft contact lenses. The build-up of bacteria and other microbes can cause adverse side effects such as contact lens acute red eye and the like. Although the problem of bacteria and other microbes is most often associated with the extended use of soft contact lenses, the build-up of bacteria and other microbes occurs for users of hard contact lens wearers as well.

Others have taught that the addition of antibacterial agents such as metal salts to contact lenses can inhibit the growth of bacteria or other microbes. See, US 2004/0150788, which is hereby incorporated by reference in its entirety. In order produce manufacturing quantities of contact lenses containing antibacterial agents, processes to prepare these lenses must give consistent results. When some of the processes disclosed in US 2004-0150788 are used with different contact lens formulations, the contact lenses that are produced have variable amounts of antibacterial agents contained therein. Since the amount of antibacterial agent in every lens must be consistent from lot to lot, it is desirable to find process to prepare contact lenses containing antibacterial agents that produce a consistent product. This need is met by the following invention.

DETAILED DESCRIPTION OF THE INVENTION

Figure 1:
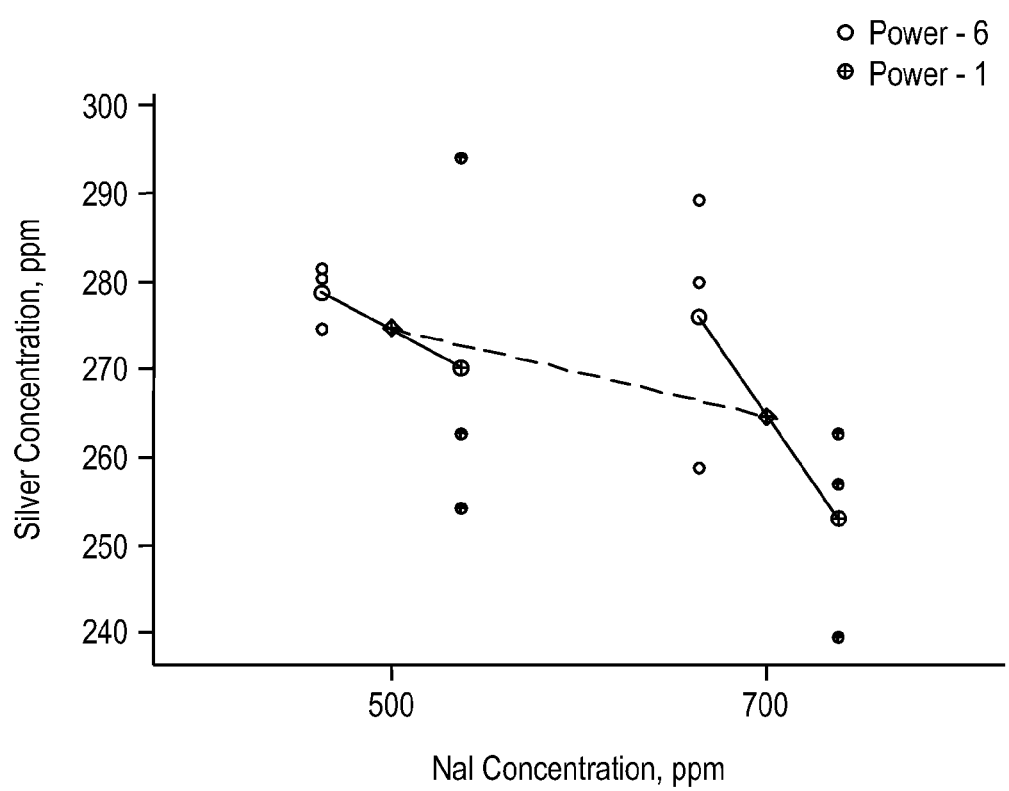
FIG. 1 Silver content vs Sodium Iodide concentration in a neutral process.

This invention includes a method of preparing an antimicrobial lens comprising, consisting essentially of, or consisting of a metal salt, wherein said method comprising the steps of
  (a) treating a cured lens, a solution comprising, consisting essentially of, or consisting of a salt precursor and an effective amount of an acidic substance, wherein the pH of said solution is less than about 7.0; and
  (b) treating the lens of step (a) with a solution comprising, consisting essentially of, or consisting of a metal agent and an effective amount of an acidic substance, wherein the pH of said solution is less than about 7.0.

As used herein, the term, "antimicrobial lens" means a lens that exhibits one or more of the following properties, the inhibition of the adhesion of bacteria or other microbes to the lenses, the inhibition of the growth of bacteria or other microbes on lenses, and the killing of bacteria or other microbes on the surface of lenses or in an area surrounding the lenses. For purposes of this invention, adhesion of bacteria or other microbes to lenses, the growth of bacteria or other microbes on lenses and the presence of bacteria or other microbes on the surface of lenses are collectively referred to as "microbial colonization." Preferably, the lenses of the invention exhibit a reduction of viable bacteria or other microbe of at least about 0.25 log, more preferably at least about 0.5 log, most preferably at least about 1.0 log (≥90% inhibition). Such bacteria or other microbes include but are not limited to those organisms found in the eye, particularly *Pseudomonas aeruginosa, Acanthamoeba species, Staphylococcus aureus, Escherichia coli, Staphylococcus epidermidis*, and *Serratia marcesens*.

As used herein, the term "acidic substance" refers to a composition may be added to a solution to reduce the pH of said solution to a pH of less than 7. Examples of acidic substances include but are not limited to acetic acid, sulfuric acid, and hydrochloric acid. The preferred acidic substance is acetic acid. The term "effective amount" refers to the concentration of the acidic substance required to reduce the pH of the solution to less than 7. It is preferable that the effective amount reduce the pH of the solution to less, than about 5, more preferably to less than about 4, most preferably less than about 3.6. The preferred acidic substance, acetic acid, is present in a concentration of about 0.01% to about 10% (weight percent, based on the total weight of the solution), more preferably about 0.5%, most preferably about 0.05%. The acidic substance in step (a) and step (b) may be the same or different. It is preferred that the acidic substance of steps (a) and (b) are the same.

As use herein, the term "metal salt" means any molecule having the general formula $[M]_a [X]_b$ wherein X contains any negatively charged ion, a is ≥1, b is ≥1 and M is any positively charged metal selected from, but not limited to, the following $Al^{+3}, Co^{+2}, Co^{+3}, Ca^{+2}, Mg^{+2}, Ni^{+2}, Ti^{+2}, Ti^{+3}, Ti^{+4}, V^{+2}, V^{+3}, Sr^{+2}, Fe^{+2}, Fe^{+3}, Ag^{+1}, Ag^{+2}, Au^{+2}, Au^{+3}, Au^{+1}, Pd^{+2}, Pd^{+4}, Pt^{+2}, Pt^{+4}, Cu^{+1}, Cu^{+2}, Mn^{+2}, Mn^{+3}, Mn^{+4}, Zn^{+2}$, and the like. Examples of X include but are not limited to $CO_3^{-2}, NO_3^{-1}, PO_4^{-3}, Cl^{-1}, I^{-1}, Br^{-1}, S^{-2}, O^{-2}$ and the like. Further X includes negatively charged ions containing $CO_3^{-2}$ $NO_3^{-1}$, $PO_4^{-3}, Cl^{-1}, I^{-1}, Br^{-1}, S^{-2}, O^{-2}$, and the like, such as $C_{1-5}alkylCO_2^{-1}$. As used herein the term metal salts does not include zeolites, disclosed in WO03/011351. This patent application is hereby incorporated by reference in its entirety. The preferred a is 1, 2, or 3. The preferred b is 1, 2, or 3. The preferred metals ions are $Mg^{+2}, Zn^{+2}, Cu^{+1}, Cu^{+2}, Au^{+2}, Au^{+3}, Au^{+1}, Pd^{+2}, Pd^{+4}, Pt^{+2}, Pt^{+4}, Ag^{+2}$, and $Ag^{+1}$. The particularly preferred metal ion is $Ag^{+1}$. Examples of suitable metal salts include but are not limited to manganese sulfide, zinc oxide, zinc sulfide, copper sulfide, and copper phosphate. Examples of silver salts include but are not limited to silver nitrate, silver sulfate, silver iodate, silver carbonate, silver phosphate, silver sulfide, silver chloride, silver bromide, silver iodide, and silver oxide. The preferred silver salts are silver iodide, silver chloride, and silver bromide.

The amount of metal in the lenses is measured based upon the total weight of the lenses. When the metal is silver, the preferred amount of silver is about 0.00001 weight percent (0.1 ppm) to about 10.0 weight percent, preferably about 0.0001 weight percent (1 ppm) to about 1.0 weight percent, most preferably about 0.001 weight percent (10 ppm) to about 0.1 weight percent, based on the dry weight of the lens. With respect to adding metal salts, the molecular weight of the metal salts determines the conversion of weight percent of metal ion to metal salt. The preferred amount of silver salt is about 0.00003 weight percent (0.3 ppm) to about 30.0 weight percent, preferably about 0.0003 weight percent (3 ppm) to about 3.0 weight percent, most preferably about 0.003 weight percent (30 ppm) to about 0.3 weight percent, based on the dry weight of the lens.

The term "salt precursor" refers to any compound or composition (including aqueous solutions) that contains a cation that may be substituted with metal ions. The concentration of salt precursor in its solution is between about 0.00001 to about 10.0 weight percent, (0.1-100,000 ppm) more preferably about 0.0001 to about 1.0 weight percent, (1-10,000 ppm) most preferably about 0.001 to about 0.1 weight percent (10-1000 ppm) based upon the total weight of the solution. Examples of salt precursors include but are not limited to inorganic molecules such as sodium chloride, sodium iodide, sodium bromide, sodium sulfide, lithium chloride, lithium iodide, lithium bromide, lithium sulfide, potassium bromide, potassium chloride, potassium sulfide, potassium iodide, rubidium iodide, rubidium bromide, rubidium chloride, rubidium sulfide, caesium iodide, caesium bromide, caesium chloride, caesium sulfide, francium iodide, francium bromide, francium chloride, francium sulfide, sodium tetrachloro argentite, and the like. Examples of organic molecules include but are not limited to tetra-alkyl ammonium lactate, tetra-alkyl ammonium sulfate, quaternary ammonium halides, such as tetra-alkyl ammonium chloride, bromide or iodide. The preferred salt precursor is selected from the group consisting of sodium chloride, sodium iodide, sodium bromide, lithium chloride, lithium sulfide, sodium sulfide, potassium sulfide, potassium iodide, and sodium tetrachloro argentite and the particularly preferred salt precursor is sodium iodide.

The term "metal agent" refers to any composition (including aqueous solutions) containing metal ions. Examples of such compositions include but are not limited to aqueous or organic solutions of silver nitrate, silver triflate, or silver acetate, silver tetrafluoroborate, silver sulfate, zinc acetate, zinc sulfate, copper acetate, and copper sulfate, where the concentration of metal agent in solution is about 1 µg/mL or greater. The preferred metal agent is aqueous silver nitrate, where the concentration of silver nitrate is the solution is about greater than or equal to 0.0001 to about 2 weight percent, more preferably about greater than 0.001 to about 0.01 weight percent based on the total weight of the solution.

The term "solution" refers to an aqueous substance such as deionized water, saline solutions, borate or buffered saline solution, or organic substance such as C1-C24 alcohols, cyclic amides, acyclic amides, ethers and acids.

The term "treating" refers to any method of contacting solutions of the metal agent and the acidic substance or, the salt precursor and the acidic substance, with the lens, where the preferred method is immersing the lens in a solution of containing either the metal agent and the acidic substance or the salt precursor and the acidic substance. Treating can include heating the lens in these solutions, but it preferred that treating is carried out at ambient temperatures. The time of treating is preferably about 1 minute to 24 hours, most preferably about 3 minute to about 30 minutes As used herein, the term "lens" refers to an ophthalmic device that resides in or on the eye. These devices can provide optical correction, wound care, drug delivery, diagnostic functionality, cosmetic enhancement or effect or a combination of these properties. The term lens includes but is not limited to soft contact lenses, hard contact lenses, intraocular lenses, overlay lenses, ocular inserts, and optical inserts. Soft contact lenses are made from silicone elastomers or hydrogels, which include but are not limited to silicone hydrogels, and fluorohydrogels.

For example the term lens includes but is not limited to those made from the soft contact lens formulations described in U.S. Pat. No. 5,710,302, WO 9421698, EP 406161, JP 2000016905, U.S. Pat. No. 5,998,498, U.S. patent application Ser. No. 09/532,943, U.S. Pat. Nos. 6,087,415, 5,760,100, 5,776,999, 5,789,461, 5,849,811, and 5,965,631. Examples of soft contact lenses formulations include but are not limited to the formulations of etafilcon A, balafilcon A, bufilcon A, deltafilcon A, droxifilcon A, phemfilcon A, ocufilicon A, perfilcon A, ocufilcon B, ocufilcon C, ocufilcon D, ocufilcon E, metafilcon A, B, vifilcon A focofilcon A, tetrafilcon B, and silicone hydrogels, as prepared in U.S. Pat. No. 5,998,498, U.S. Ser. No. 09/532,943, a continuation-in-part of U.S. patent application Ser. No. 09/532,943, filed on Aug. 30, 2000, WO03/22321, U.S. Pat. Nos. 6,087,415, 5,760,100, 5,776,999, 5,789,461, 5,849,811, and 5,965,631. These patents as well as all other patent disclosed in this paragraph are hereby incorporated by reference in their entirety.

Lenses of the invention may be made from silicone hydrogel components. A silicone-containing component is one that contains at least one [—Si—O—Si] group, in a monomer, macromer or prepolymer. Preferably, the Si and attached O are present in the silicone-containing component in an amount greater than 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, N-vinyl lactam, N-vinylamide, and styryl functional groups. Examples of silicone components which may be included in the silicone hydrogel formulations include, but are not limited to silicone macromers, prepolymers and monomers. Examples of silicone macromers include, without limitation, polydimethylsiloxane methacrylated with pendant hydrophilic groups as described in U.S. Pat. Nos. 4,259,467; 4,260,725 and 4,261,875; polydimethylsiloxane macromers with polymerizable functional zo group(s) described in U.S. Pat. Nos. 4,136,250; 4,153,641; 4,189,546; 4,182,822; 4,343,927; 4,254,248; 4,355,147; 4,276,402; 4,327,203; 4,341,889; 4,486,577; 4,605,712; 4,543,398; 4,661,575; 4,703,097; 4,837,289; 4,954,586; 4,954,587; 5,346,946; 5,358,995; 5,387,632; 5,451,617; 5,486,579; 5,962,548; 5,981,615; 5,981,675; and 6,039,913; polysiloxane macromers incorporating hydrophilic monomers such as those described in U.S. Pat. Nos. 5,010,141; 5,057,578; 5,314,960; 5,371,147 and 5,336,797; macromers comprising polydimethylsiloxane blocks and polyether blocks such as those described in U.S. Pat. Nos. 4,871,785 and 5,034,461, combinations thereof and the like. All of the patents cited herein are hereby incorporated in their entireties by reference.

The silicone and/or fluorine containing macromers described in U.S. Pat. Nos. 5,760,100; 5,776,999; 5,789,461; 5,807,944; 5,965,631 and 5,958,440 may also be used. Suitable silicone monomers include tris(trimethylsiloxy)silylpropyl methacrylate, hydroxyl functional silicone containing monomers, such as 3-methacryloxy-2-hydroxypropyloxy) propylbis(trimethylsiloxy)methylsilane and those disclosed in WO03/22321, and mPDMS containing or the siloxane monomers described in U.S. Pat. Nos. 4,120,570, 4,139,692, 4,463,149, 4,450,264, 4,525,563; 5,998,498; 3,808,178; 4,139,513; 5,070,215; 5,710,302; 5,714,557 and 5,908,906.

Additional suitable siloxane containing monomers include, amide analogs of TRIS described in U.S. Pat. No. 4,711,943, vinylcarbamate or carbonate analogs described in U.S. Pat. No. 5,070,215, and monomers contained in U.S. 6,020,445, monomethacryloxypropyl terminated polydimethylsiloxanes, polydimethylsiloxanes, 3-methacryloxypropylbis(trimethylsiloxy)methylsilane, methacryloxypropylpentamethyl disiloxane and combinations thereof.

In addition to soft contact lens formulations, hard contact lenses may be used. Examples of hard contact lens formulations are made from polymers that include but are not limited to polymers of poly(methyl)methacrylate, silicon acrylates, silicone acrylates, fluoroacrylates, fluoroethers, polyacetylenes, and polyimides, where the preparation of representative examples may be found in JP 200010055, JP 6123860 and U.S. Pat. No. 4,330,383. Intraocular lenses of the invention can be formed using known materials. For example, the lenses may be made from a rigid material including, without limitation, polymethyl methacrylate, polystyrene, polycarbonate, or the like, and combinations thereof. Additionally, flexible materials may be used including, without limitation, hydrogels, silicone materials, acrylic materials, fluorocarbon materials and the like, or combinations thereof. Typical intraocular lenses are described in WO 0026698, WO 0022460, WO 9929750, WO 9927978, WO 0022459, and JP 2000107277. U.S. Pat. Nos. 4,301,012; 4,872,876; 4,863, 464; 4,725,277; 4,731,079. All of the references mentioned in this application are hereby incorporated by reference in their entirety.

Preferably, the lenses of the invention are optically clear, with optical clarity comparable to lenses such as lenses made from etafilcon A, genfilcon A, galyfilcon A, lenefilcon A, polymacon, acquafilcon A, balafilcon A, and lotrafilcon A. The most preferred lens formulations are those used to prepare ionic lenses. Monomers that are useful in the preparation of such lenses include methacrylic acid and the like. Examples of the most preferred lens formulations include those used to prepare etafilcon A, balafilcon A, bufilcon A, deltafilcon A, droxifilcon A, phemfilcon A, ocufilicon A, perfilcon A, ocufilcon B, ocufilcon C, ocufilcon D, ocufilcon E, metafilcon A, B, vifilcon A focofilcon A, and tetrafilcon B Many of the lens formulations cited above may allow a user to insert the lenses for a continuous period of time ranging from one day to thirty days. It is known that the longer a lens is on the eye, the greater the chance that bacteria and other microbes will build up on the surface of those lenses. Therefore there is a need to develop lenses that release antimicrobial agents such as silver, over an extended period of time.

The term "cured" refers to any of a number of methods used to react a mixture of lens components (ie, momoner, prepolymers, macromers and the like) to form lenses. Lenses can be cured by light or heat. The preferred method of curing is with radiation, preferably UV or visible light, and most preferably with visible light. The lens formulations of the present invention can be formed by any of the methods know to those skilled in the art, such as shaking or stirring, and used to form polymeric articles or devices by known methods.

For example, the antimicrobial lenses of the invention may be prepared by mixing reactive components and any diluent(s) with a polymerization initator and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the lens formulation in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197, 266. The preferred method for producing antimicrobial lenses of this invention is by molding. In the case of hydrogel lenses, for this method, the lens formulation is placed in a mold having the approximate shape of the final desired lens and the lens formulation is subjected to conditions whereby the components polymerize, to produce a hardened disc that is subjected to a number of different processing steps including treating the polymerized lens with liquids (such as water, inorganic salts, or organic solutions) to swell, or otherwise equilibrate this lens prior to enclosing the lens in its final packaging. This method is further described in U.S. Pat. Nos. 4,495,313; 4,680,336; 4,889,664; and 5,039,459, incorporated herein by reference. Polymerized lenses that have not been swelled or otherwise equilibrated are considered cured lenses for purposes of this invention.

Further, the invention includes a method of preparing an antimicrobial lens comprising, consisting essentially of, or consisting of a metal salt, wherein the method comprises, consists essentially of, or consists of the steps of
  (a) treating a cured lens, a solution comprising, consisting essentially of, or consisting of a metal agent and an effective amount of an acidic substance, wherein the pH of said solution is less than about 7.0; and
  (b) treating the lens of step (a) with a solution comprising, consisting essentially of, or consisting of a salt precursor and an effective amount of an acidic substance, wherein the pH of said solution is less than about 7.0.

The terms antimicrobial lens, metal salt, salt precursor, metal agent, effective zo amount and treating all have their aforementioned meanings and preferred ranges.

Still further the invention includes an antimicrobial lens comprising, consisting essentially of, or consisting of a metal salt, prepared by a method comprising the steps of
  (a) treating a cured lens, a solution comprising, consisting essentially of, or consisting of a salt precursor and an effective amount of an acidic substance, wherein the pH of said solution is less than about 7.0; and
  (b) treating the lens of step (a) with a solution comprising, consisting essentially of, or consisting of a metal agent and an effective amount of an acidic substance, wherein the pH of said solution is less than about 7.0.

The terms antimicrobial lens, metal salt, salt precursor, metal agent, effective amount and treating all have their aforementioned meanings and preferred ranges.

Yet still further, the invention includes an antimicrobial lens comprising, consisting essentially of, or consisting of a metal salt, prepared by a method comprising the steps of
  (a) treating a cured lens, a solution comprising, consisting essentially of, or consisting of a metal agent and an effective amount of an acidic substance, wherein the pH of said solution is less than about 7.0; and
  (b) treating the lens of step (a) with a solution comprising, consisting essentially of, or consisting of a salt precursor and an effective amount of an acidic substance, wherein the pH of said solution is less than about 7.0.

The terms antimicrobial lens, metal salt, salt precursor, metal agent, effective amount and treating all have their aforementioned meanings and preferred ranges.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLES

The following abbreviations were used in the examples
Blue HEMA=the reaction product of reactive blue number 4 and HEMA, as described in Example 4 or U.S. Pat. No. 5,944,853
CGI 819=bis(2,4,6-trimethylbenzoyl)phenylphosphineoxide
DI water=deionized water
DMA=N,N-dimethylacrylamide
HEMA=hydroxyethyl methacrylate
MAA=methacrylic acid;
mPDMS=mono-methacryloxypropyl terminated polydimethylsiloxane (MW 800-1000)
acPDMS=bis-3-acryloxy-2-hydroxypropyloxypropyl polydimethylsiloxane
Norbloc=2-(2'-hydroxy-5-methacrylyloxyethylphenyl)-2H-benzotriazole
ppm=parts per million micrograms of sample per gram of dry lens
PVP=polyvinylpyrrolidinone (360,000 or 2,500)
Simma 2=3-methacryloxy-2-hydroxypropyloxy)propylbis(trimethylsiloxy)methylsilane
TAA=t-amyl alcohol
Sodium Sulfate Packing Solution (SSPs)
SSPS contains the following in deionized $H_2O$:
1.40 weight % sodium sulfate
0.185 weight % sodium borate [1330-43-4], Mallinckrodt
0.926 weight % boric acid [10043-35-3], Mallinckrodt
0.005 weight % methylcellulose
Preparation Lens Type A
A hydrogel blend was made from the following monomer mix (all amounts were calculated as weight percent: 30.00% SIMAA 2, 28.0% mPDMS, 5.0% acPDMS, 19.0% DMA, 7.15% HEMA, 1.60% MAA, 7.00% PVP 360,000, 2.0% Norbloc, 1.0% CGI 819 and 0.02% Blue HEMA, 60 weight percent of the preceding component mixture was further diluted with diluent, 40 weight percent of 72.5:27.5 TAA: PVP 2,500, to form the final monomer mix. The blend placed in a two part contact lens mold and was cured using the following sequential conditions a) room temperature for 30 seconds using a visible light that emits 1 mW/sq cm, b) 75° C. 120 seconds, c) 75° C. 120 seconds 1.8 mW/sq/cm, and d) 75° C. 240 seconds 6.0 mW/sq cm. The cured lenses are removed from the molds and hydrated with DI.

Example 1

Preparation of Antimicrobial Lenses from Cured Lenses without an Acidic Substance Cured and hydrated lenses of Type A are placed in a jar with sodium iodide solution in deionized water (500-700 ppm), containing 50 ppm of methylcellulose (~3 mL solution per lens,) and rolled on a jar roller overnight. The lenses were transferred from the jar to a blister pack where the excess sodium iodide solution was removed. A solution (800 µL, 150 ppm) of silver nitrate in deionized water, containing the appropriate dispersion agent, was added to the blister for two to five minutes. The silver nitrate solution was removed, and the lenses were placed in a jar containing deionized water and rolled on a jar roller for approximately thirty minutes. The deionized water was replaced with borate buffered sodium sulfate solution containing 50 ppm methylcellulose water (SSPS), and allowed to roll on the jar roller for an additional 30 minutes. The solution was then replaced with fresh SSPS.

The lenses were then transferred to new blisters and dosed with 950 µL of SSPS. The blisters were sealed and autoclaved at 125° C. for 18 minutes and analyzed for silver content using the method described below. The results are presented in FIG. 1. This data shows that increasing the concentration of sodium iodide, unexpectedly reduces the amount of silver iodide deposited into the lens.

Silver content of the lenses after lens autoclaving was determined by Instrumental Neutron Activation Analysis "INAA". INAA is a qualitative and quantitative elemental analysis method based on the artificial induction of specific radionuclides by irradiation with neutrons in a nuclear reactor. Irradiation of the sample is followed by the quantitative measurement of the characteristic gamma rays emitted by the decaying radionuclides. The gamma rays detected at a particular energy are indicative of a particular radionuclide's presence, allowing for a high degree of specificity. Becker, D. A.; Greenberg, R. R.; Stone, S. F. J. Radioanal. Nucl. Chem. 1992, 160(1), 41-53; Becker, D. A.; Anderson, D. L.; Lindstrom, R. M.; Greenberg, R. R.; Garrity, K. M.; Mackey, E. A. J. Radioanal. Nucl. Chem. 1994, 179(1), 149-54. The INAA procedure used to quantify silver content in contact lens material uses the following two nuclear reactions:
1. In the activation reaction, $^{110}Ag$ is produced from stable $^{109}Ag$ (isotopic abundance=48.16%) after capture of a radioactive neutron produced in a nuclear reactor.
2. In the decay reaction, $^{110}Ag$ ($\tau^{1/2}$=24.6 seconds) decays primarily by negatron emission proportional to initial concentration with an energy characteristic to this radionuclide (657.8 keV).

The gamma-ray emission specific to the decay of $^{110}Ag$ from irradiated standards and samples are measured by gamma-ray spectroscopy, a well-established pulse-height analysis technique, yielding a measure of the concentration of the analyte.

Example 2

Preparation of Antimicrobial Lenses From Cured Lenses With an Acidic Substance

Figure 2:
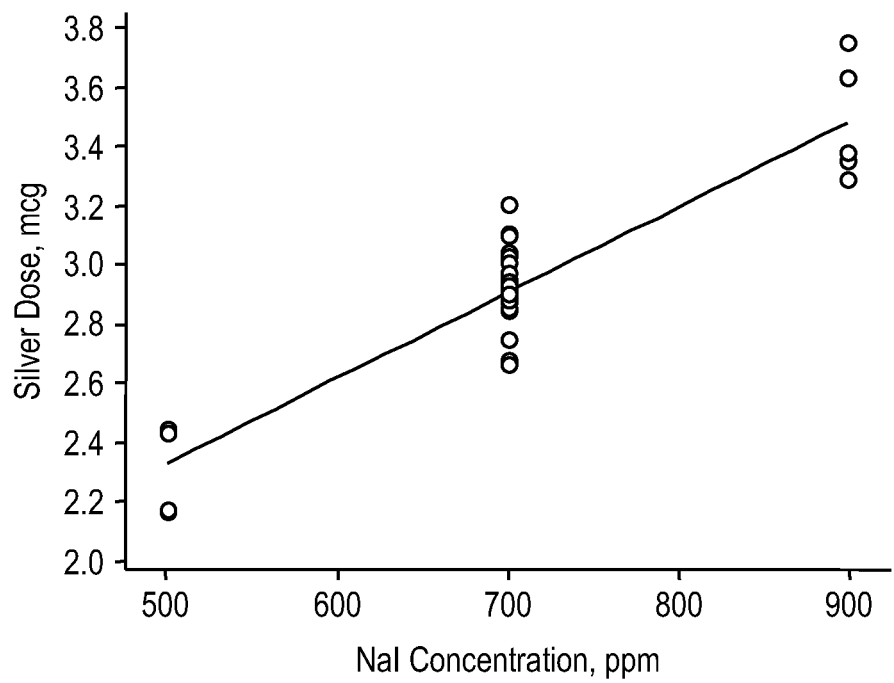
FIG. 2. Silver content vs Sodium Iodide in an acidified process.

The procedure of Example 1 was repeated with one exception, 0.05% weight percent of Acetic Acid in deionized water was added to the sodium iodide solution and the silver nitrate solution. The lenses were analyzed for silver content and the data is presented in FIG. 2. This data shows that the acidified process gives the expected increase in the amount of silver iodide deposited in the lens as the amount of sodium iodide is increased.

What is claimed is:
1. A method of preparing an antimicrobial lens comprising a metal salt, wherein said method comprising the steps of
   (a) treating a cured lens, with a solution comprising, a salt precursor and an effective amount of an acidic substance, wherein the pH of said solution is less than 7.0; and
   (b) treating the lens of step (a) with a solution comprising, consisting essentially of, or consisting of a metal agent and an effective amount of an acidic substance, wherein the pH of said solution is less than 7.0.

2. The method of claim 1 wherein the acidic substance is selected from the group consisting of acetic acid, hydrochloric acid, and sulfuric acid.

3. The method of claim 1 wherein the acidic substance is acetic acid.

4. The method of claim 1 wherein the effective amount of the acidic substance is about 0.01% to about 10%.

5. The method of claim 1 wherein the effective amount of the acidic substance is about 0.5%.

6. The method of claim 1 wherein the effective amount of the acidic substance is about 0.05%.

7. The method of claim 1 wherein the ph of the solution of steps (a) and (b) is about 2 to about 5.

8. The method of claim 1 wherein the ph of the solution of steps (a) and (b) is about 2 to about 4.

9. The method of claim 1 wherein the pH of the solution of steps (a) and (b) is about 3 to about 4.

10. The method of claim 1 wherein the salt precursor is selected from the group consisting of tetra-alkyl ammonium lactate, tetra-alkyl ammonium sulfate, tetra-alkyl ammonium chloride, tetra-alkyl ammonium, bromide, tetra-alkyl ammonium iodide, sodium chloride, sodium iodide, sodium bromide, lithium chloride, lithium sulfide, sodium sulfide, potassium sulfide, and sodium tetrachloro argentate.

11. The method of claim 1 wherein the salt precursor is selected from the group consisting of sodium chloride, sodium iodide, sodium bromide, lithium chloride, lithium sulfide, sodium sulfide, potassium sulfide, and sodium tetrachloro argentite.

12. The method of claim 1 wherein the salt precursor is sodium iodide.

13. The method of claim 1 wherein the metal salt is selected from the group consisting of silver iodide, silver chloride, and silver bromide.

14. The method of claim 1 wherein the metal agent is selected from the group consisting of silver nitrate, silver triflate, and silver acetate.

15. The method of claim 1 wherein the metal agent is silver acetate.

16. A method of preparing an antimicrobial lens comprising a metal salt, wherein said method comprising the steps of
   (a) treating a cured lens, with a solution comprising, a metal agent and an effective amount of an acidic substance, wherein the pH of said solution is less than 7.0; and
   (b) treating the lens of step (a) with a solution comprising, consisting essentially of, or consisting of a salt precursor and an effective amount of an acidic substance, wherein the pH of said solution is less than 7.0.

* * * * *